(12) United States Patent
Wolinsky et al.

(10) Patent No.: US 6,699,186 B1
(45) Date of Patent: Mar. 2, 2004

(54) METHODS AND APPARATUS FOR DEPLOYING AND IMPLANTABLE BIOSENSOR

(75) Inventors: Lone Wolinsky, Ramat Gan (IL); Avi Penner, Tel Aviv (IL)

(73) Assignee: Remon Medical Technologies LTD (IL)

( * ) Notice: Subject to any disclaimer, the term of this patent is extended or adjusted under 35 U.S.C. 154(b) by 0 days.

(21) Appl. No.: 09/523,414

(22) Filed: Mar. 10, 2000

(51) Int. Cl.[7] ............................................... A61B 5/00
(52) U.S. Cl. ..................................................... 600/300
(58) Field of Search ................................ 600/300, 317, 600/454, 504, 505; 623/1.11; 606/195, 213; 604/514, 11, 285, 57

(56) References Cited

U.S. PATENT DOCUMENTS

| | | | | |
|---|---|---|---|---|
| 4,900,303 A | * | 2/1990 | Lemelson | 604/514 |
| 5,772,669 A | * | 6/1998 | Vrba | 623/1.11 |
| 5,833,603 A | * | 11/1998 | Kovacs et al. | 600/317 |
| 5,967,986 A | * | 10/1999 | Cimochowski et al. | 600/454 |

FOREIGN PATENT DOCUMENTS

WO    WO 83/03348 A1    10/1983

* cited by examiner

Primary Examiner—Max F. Hindenburg
Assistant Examiner—Brian Szmal
(74) Attorney, Agent, or Firm—Bingham McCutchen LLP

(57) ABSTRACT

An implantation device for delivering a biosensor to an implantation site in a patient's body comprises an elongate catheter equipped with a distally located cavity sized to house a biosensor. Once the distal end of the catheter is positioned adjacent the implantation site, the biosensor is released through an opening from the cavity into the site. A removable cover, such as a thin adhesive film, may be used to retain the biosensor in the cavity, while the catheter is guided through the body to the implantation site. The implantation device may include an actuator for displacing the biosensor from the cavity into the implantation site. By way of one example, the actuator may be a piston inserted through a lumen of the catheter.

31 Claims, 7 Drawing Sheets

METHODS AND APPARATUS FOR DEPLOYING AND IMPLANTABLE BIOSENSOR

FIELD OF INVENTION

The present invention pertains generally to the field of implantable biosensors and, in particular, to methods and apparatus for locating a biosensor at an implantation site in the body for monitoring physiological conditions in a patient.

BACKGROUND

An aneurysm is an abnormal ballooning of the wall of an artery that results from the weakening of the artery due to injury, infection, or other conditions, such as a congenital defect in the arterial connective tissue. Common forms of such an aneurysm include an abdominal aortic aneurysm, an iliac aneurysm, a bifurcated aneurysm of the abdominal aorta and the iliac, and a thoracic aortic aneurysm.

The aorta, which is the main arterial link in the circulatory system, begins at the left ventricle of the heart, forms an arch above the heart, and passes behind the heart, continuing downward through the thorax and the abdomen. Along this path, the abdominal aorta branches into two vessels, called the renal arteries, that supply blood to the kidneys. Below the level of the renal arteries, the abdominal aorta extends approximately to the level of the fourth lumbar vertebra, where it branches into the iliac arteries. The iliac arteries, in turn, supply blood to the lower extremities and the perineal region.

Abdominal aortic aneurysms can occur in the portion of the abdominal aorta between the renal and the iliac arteries. This condition, which is most often seen in elderly men, often leads to serious complications, including rupture of the aneurysmal sac. A ruptured aneurysm occurs in approximately 3.6 out of 10,000 people and is considered a medical emergency, since the resultant rapid hemorrhaging is frequently fatal.

There are generally two methods for treating abdominal aortic aneurysms: (1) surgical repair of the aneurysm, and (2) endoluminal stent graft implantation. Surgical repair of the aneurysm involves the implantation of a tubular prosthetic vascular graft, traditionally made of fluoropolymers, such as polytetrafluoroethylene (PTFE) or polyester (Dacron), into the aorta. These prosthetic vascular grafts traditionally have been implanted by open surgical techniques, whereby a diseased or damaged segment of the blood vessel is surgically cut along its longitudinal axis and the tubular bioprosthetic graft is then inserted coaxial to the original artery and anastomosed within the host blood vessel as an internal replacement for the diseased segment. Then the longitudinal cut in the artery is sutured. Alternatively, prosthetic vascular grafts have been used as bypass grafts wherein opposite ends of the graft are sutured to the host blood vessel in order to form a conduit around the diseased, injured, or occluded segment of the host vessel.

These surgical approaches suffer from similar disadvantages, namely, the extensive recovery period associated with major abdominal surgery, the difficulties in suturing the graft to the aorta, the unsuitability of surgery for many at-risk patients, and the high mortality and morbidity rates associated with surgical intervention of this magnitude.

The second approach to treating an abdominal aortic aneurysm, endolumenal stent graft implantation, overcomes many of these disadvantages. An endoluminal stent graft normally consists of a vascular graft that is supported by a metallic stent skeleton over a portion of the length of the graft. By introducing and deploying the stent graft through the lumen of the blood vessel, a surgeon may then repair the damaged aortic segment using only percutaneous or minimal incisions in the patient. This technique initially involves translumenal delivery of the graft in a compacted low profile configuration by way of a catheter or some other translu minally advancable delivery apparatus. The stent is then radially expanded, thereby anchoring the graft to the surrounding blood vessel wall and sealing off the aneurysm from the rest of the circulatory system. As a result, the pressure within the isolated aneurysmal sac and the endotension of the artery are both reduced.

It is generally agreed that such endoluminal stent grafts work best in patients with small- to medium-sized abdominal aortic aneurysms, or in patients with large abdominal aortic aneurysms who are characterized as high risk candidates for open surgical abdominal aortic aneurysm repair. In addition to treating vascular aneurysms, an endovascular stent graft may also be used to treat occlusive vascular disease.

In some instances, the stented graft is constructed in such a manner that the tubular graft material forms a complete barrier between the stent and the blood, which is flowing through the blood vessel. In this way, the tubular graft material serves as a smooth, biologically compatible inner lining for the stent. Graft material known in the prior art includes woven or knitted fabrics, such as polyester fiber, or a porous form of PTFE known as ePTFE.

The major complication involved in the endolumenal stent graft implantation is the formation of an endoleak. An endoleak is defined as blood leakage into the aneurysmal sac causing the sac to fill with blood and increasing the endotension. Endotension is defined by the internal pressure within the aneurysm, the aneurysm diameter and wall thickness. In particular, endotension is a physical parameter that indicates the chances of aneurysm rupture. The implantation of a stent graft prevents blood from filling the aneurysmal sac, resulting in a depressurization of the sac with minimal influence on the aneurysm wall thickness. The diameter of the aneurysm might change with pressure reduction, but the direct parameter that varies is the pressure.

Endoleaks can be divided into four categories: Type I, which results from leakage due to insufficient sealing of the graft against the aortic wall; type II, which results from blood flow to the aneurysmal sac through bypass arteries; type III, which arises from mechanical failure of the graft system; and type IV, which arises from leakage through the graft fabric due to the porosity of the material.

Because of the high risk of aneurysmal rupture, the early detection of endoleaks resulting in endotension is crucial. With early detection, the pressure within the aneurysmal sac may be reduced through endovascular treatment (balloon inflation or additional stent graft implantation for improve sealing) or a surgical intervention. Currently, the standard method for the detection of endoleaks is through contrast-enhanced computerized tomography (CT), which relies on the x-ray imaging of the abdominal region after injection of a contrast media in order to improve the detection of blood and vascular tissue. If an endoleak is present, then the aneurysmal sac will fill with contrast media and the endoleak will then be identified in the resultant CT scan.

Although CT scans are considered a reliable method for detecting endoleaks, they suffer from several disadvantages.

First, CT scans require an experienced operator and an expensive apparatus, placing significant financial constraints on its frequency of use. Second, the CT scan procedure exposes the patient to x-ray radiation and thus cannot be used as frequently as desired. Third, CT scans can only provide an estimate of the pressure within the aneurysm indirectly by detecting leakage into the aneurysmal sac, and are unable to detect small leaks that may cause slow, but potentially dangerous, pressurization within the aneurysm.

In addition to CT scans, ultrasound imaging methods have also been used to detect endoleaks. Ultrasound-based methodologies posses several advantages over CT, including a simpler apparatus and the absence of ionizing radiation. Consequently, such imaging can be performed more often and at a lower cost than CT scans. However, ultrasound-based imaging is operator dependent and less reliable than CT scans.

Thus, there exists a need for more accurate and reliable methods and apparatus for detecting endoleaks. More particularly, there exists a need for directly monitoring the internal pressure within an aneurysmal sac in order to determine the presence or absence of an endoleak or endotension at a higher frequency.

SUMMARY OF THE INVENTION

In accordance with one aspect of the invention, a device for delivering a biosensor to an implantation site in a body is provided, comprising an elongate catheter comprising a recess configured to carry the biosensor while the catheter is guided to the implantation site. In one preferred embodiment, the recess comprises a longitudinal indentation etched or otherwise formed in a side of the catheter. In another preferred embodiment, the recess comprises a circumferential indentation formed in a side of the catheter. In still another preferred embodiment, the recess comprises a cavity formed in the catheter. In yet another preferred embodiment, the recess comprises a cavity formed in a distal tip of the catheter.

In preferred embodiments, the implantation device may also include a retaining element configured to retain the biosensor in the recess. In one preferred embodiment, the retaining element comprises a thin membrane at least partially covering the recess. In another preferred embodiment, the retaining element comprises a retractable sheath extending out of a distal opening of the catheter. In yet another preferred embodiment, the retaining element comprises a retractable filament inserted through a distal opening of the catheter. A clamping mechanism may also be provided, which is adapted to secure the retaining element against the catheter. By way of one non-limiting example, the clamping mechanism may comprise a sleeve circumferentially attached to the catheter.

In preferred embodiments, the implantation device may also include an actuator disposed in, or adjacent to, the recess, the actuator configured to eject the biosensor from the recess. By way of non limiting examples, the actuator may comprise a piston or a spring. In one preferred embodiment, the actuator comprises a protrusion located in, or adjacent to, the recess, which is positioned to displace the biosensor from the recess. The implantation device may also be provided with a handle assembly associated with the actuator, the actuator being controllable by manipulation of the handle assembly.

In accordance with another aspect of the invention, a method for using an implantation device to deliver a biosensor to an implantation site in a body is provided, the implantation device comprising an elongate catheter having a distally located recess configured to carry the biosensor, the method including the steps of introducing the catheter into the body with the biosensor disposed in the recess, until the recess is positioned at the implantation site, and then displacing the biosensor from the recess into the implantation site.

In preferred implementations of the method, the implantation device includes an actuator disposed in, or adjacent to, the recess, wherein the ejecting step is performed with the actuator. In one preferred implementation of the method, the implantation device further includes a thin membrane at least partially covering the recess, wherein the actuator, during the ejecting step, causes the biosensor to be pushed through the thin membrane and into the implantation site. In another preferred implementation of the method, the implantation device further includes a retractable retaining element configured to retain the biosensor in the recess during the introducing step. In accordance with yet another aspect of the invention, the catheter of the implantation device is guided to the implantation site in conjunction with the delivery of a stent graft.

Notably, the implantation site may be an abdominal aortic aneurysm, in the iliac of a bifurcated abdominal aortic aneurysm, or a thoracic aortic aneurysm, or some combination thereof. As will be appreciated by those skilled in the art, however, the inventive aspects disclosed and described may be applied to the placement of a biosensor in any implantation site in a body, and are not restricted to abdominal or aneurysmal implantation sites.

In accordance with still another aspect of the invention, a method using an implantation device for delivering a biosensor to an implantation site in a body is provided, the implantation device comprising an elongate catheter having a distally located recessed area configured to house the biosensor, and a retractable retaining element configured to retain the biosensor in the recessed area, the method including introducing the catheter into the body, with the biosensor retained in the recessed area by the retaining element, until the recessed area is positioned at the implantation site, and retracting the retaining element so that the biosensor may move freely from the recessed area into the implantation site.

In accordance with yet another aspect of the invention, a method using an implantation device for delivering a biosensor to an implantation site in a body is provided, the implantation device comprising an elongate catheter having a distally located recess configured to at least partially house the biosensor, a retractable cover member configured to retain the biosensor within the recess, and an actuator configured to displace the biosensor from the recess, the method including introducing the catheter into the body with the biosensor retained within the recess by the cover member, until the recess is positioned at the implantation site, retracting the cover member to allow passage of the biosensor from the recess, and ejecting the biosensor from the recess into the implantation site with the actuator.

As will be apparent to those skilled in the art, other and further aspects of the present invention will appear hereinafter.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
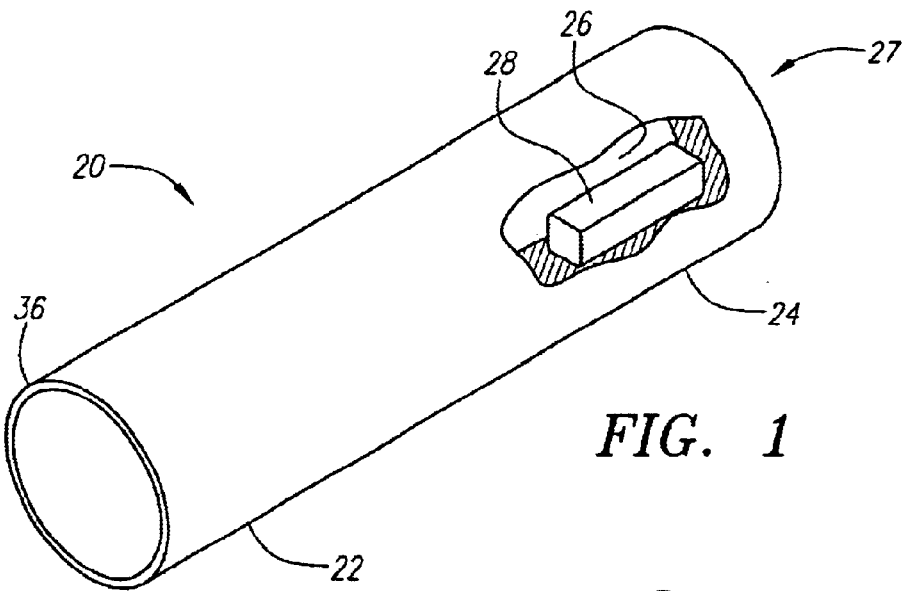
FIG. 1 is a perspective view of a distal portion of a first preferred embodiment of a biosensor implantation device constructed in accordance with the present invention.
Figure 2:
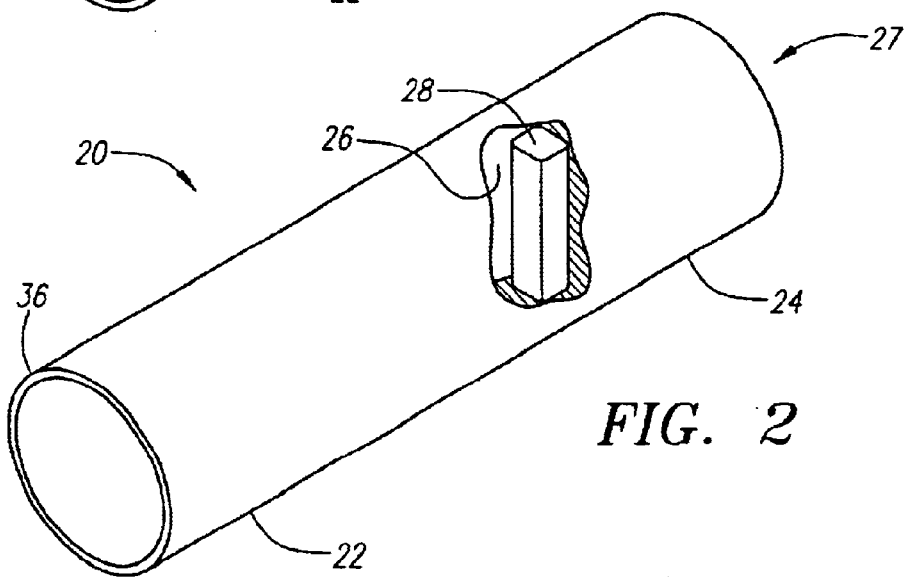
FIG. 2 is a perspective view of a distal portion of another preferred embodiment of a biosensor implantation device constructed in accordance with the present invention.
Figure 3:
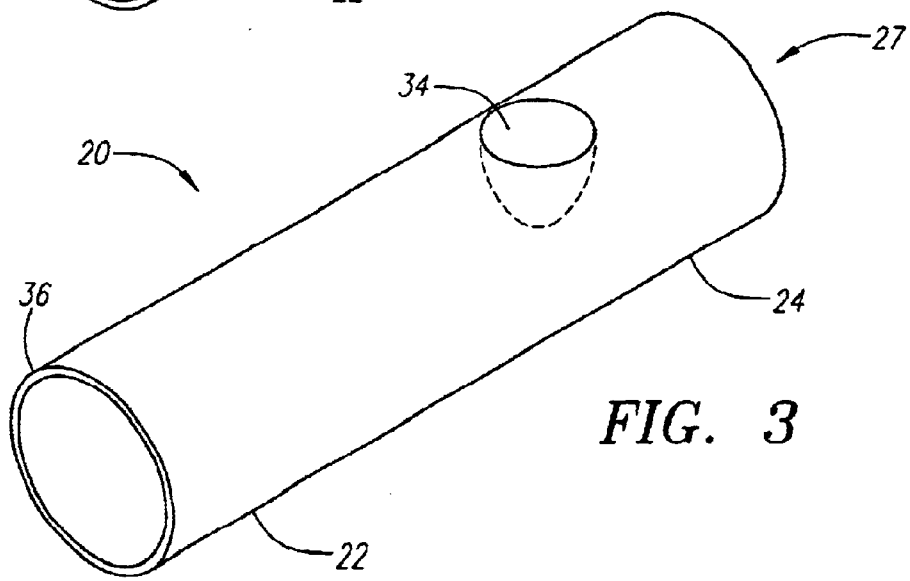
FIG. 3 is a perspective view of a distal portion of still another preferred embodiment of a biosensor implantation device constructed in accordance with the present invention.

Referring to FIGS. 1–3, a preferred biosensor implantation device 20 comprises an elongate catheter 22 having an indentation, or recess 26 etched or otherwise formed in an outer wall 24 of a distal end 27 of the catheter 22. The recess 26 is sized to carry a biosensor device 28 while the catheter distal end 27 is guided to an implantation site in a body. In particular, the recess 26 is sized to carry the biosensor 28 without any substantial increase in the overall profile (i.e., outer dimension) of the catheter 22. Depending on the dimension of the catheter 22, as well as the dimensions of the particular biosensor 28, the recess may be disposed longitudinally, as shown in FIG. 1, circumferentially, as shown in FIG. 2, or at some intermediate orientation. The recess 26 may be slight in depth as compared to the overall profile of the catheter 22, or may be a deep cavity 34 formed in the catheter wall, as shown in FIG. 3.

Figure 4:
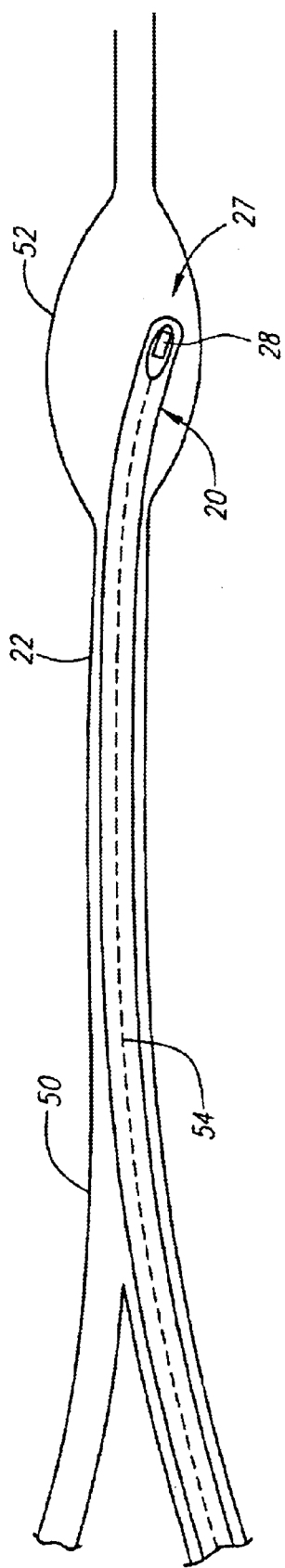
FIG. 4 is a diagrammatic view of a blood vessel including an aneurysml sac, and depicting an exemplary implantation device constructed in accordance with the present invention positioned to deploy a biosensor within the aneurysmal sac.

FIG. 4 shows an exemplary blood vessel 50, including an aneurysmal sac 52. In accordance with a general aspect of the invention, the implantation device 20 is guided through the blood vessel 50 via a guide wire 54 inserted through an internal lumen of the catheter 22. The catheter 22 is preferably coated with a relatively thin layer 36, e.g., fifty microns or less, of a smooth polymer, such as silicone, to enhance its bio-compatibility and ease of insertion through the blood vessel 50. In particular, the distal end 27 of the implantation device 20 is guided to the aneurysmal sac 52, wherein a biosensor 28 carried in the recess 26 is passively (or actively) deployed from the recess 26 into the aneurysmal sac 52. Notably, the implantation device 20 may be used to deposit more than one biosensor during a single deployment step.

By way of example only, the aneurysmal sac 52 may include an abdominal or thoracic aortic aneurysm, in which case the implantation device 20 may be used to deploy one or more biosensors 28 in combination with the delivery of a stent graft (not shown). As will be appreciated by those skilled in the art, however, the inventive aspects disclosed and described may be applied to the placement of a biosensor 28 in any implantation site in a body that is accessible by guiding the distal tip of the deployment catheter 22.

Depending on the particular implementation site and needs of the patient, each biosensor 28 may comprise any of a number of sensor types, such as a sensor selected from the group consisting of a pressure sensor, a temperature sensor, a position sensor, a tactility sensor, an electrical impedance sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electrical energy sensor, an electromagnetic field sensor, a chemical sensor, an ionic sensor, and an enzymatic sensor.

In preferred embodiments, the biosensor 28 employs wireless telemetry to deliver information from the implantation site to an instrument external to the body. Further, the biosensor may or may not require a battery. For example, one preferred biosensor 28 is constructed in accordance with the teachings of U.S. patent application Ser. No. 09/303,644, which is fully incorporated by reference for all that it teaches and discloses. As taught therein, an acoustic telemetry biosensor includes means for converting acoustic energy received from an externally originated interrogation signal into a current supply for powering one or more sensors embedded in the biosensor for measuring various biological parameters at the implantation site. The biosensor further includes means for modulating the interrogation signal to transmit the measured information external to the body.

In another preferred embodiment, the biosensor 28 is constructed in accordance with the teachings of U.S. Pat. No. 5,704,352, which is also fully incorporated by reference for all that it teaches and discloses. Other biosensor constructions are also possible and will be known to those skilled in the art.

Figure 5:
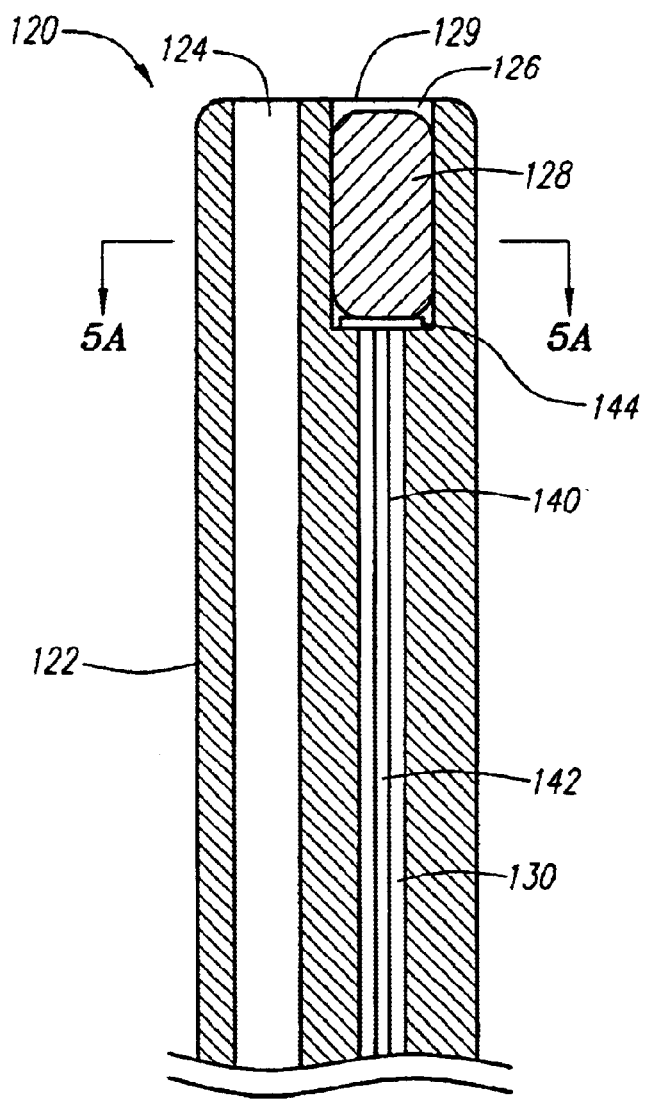
FIG. 5 is a cut-away side view of a distal portion of a still further preferred embodiment of an implantation device constructed in accordance with the present invention.
Figure 5A:
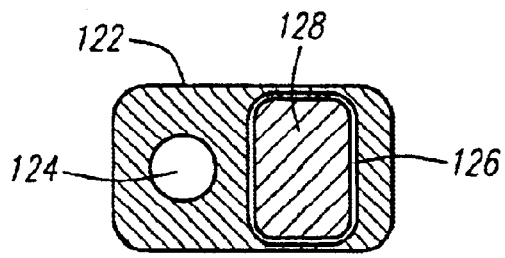
FIG. 5A is a cut-away cross section of the implantation device, taken along lines A—A of FIG. 5.

By way of illustration, FIGS. 5 and 5A, show a further preferred biosensor implantation device 120, constructed in accordance with the present invention. The implantation device 120 comprises an elongate catheter 122 including at least one lumen 124, a distal recess 126 for housing a biosensor 128, and an actuator 140. The catheter 122 may be guided to a desired implantation site by way of a guide wire (not shown) that is inserted through the lumen 124. Various other means of guiding the catheter 122 to an intended implantation site are known to those skilled in the art and are contemplated within the scope of the invention.

The actuator 140 is operative to deploy or eject the biosensor 128 from the recess 126, once the distal end of the catheter 122 is guided to a desired implantation site in a patient's body. The actuator 140 includes a piston 142 that extends through a second lumen 130 of the catheter 122, and a plunger 144 that rests within the recess 126. The plunger 144 may have an enlarged surface area on a distal end of the piston 142 for actively deploying (i.e., ejecting) the biosensor 128 out of the recess 126 and into the implantation site. Preferably the piston 142 extends to a proximal end of the catheter 122, thereby enabling a user to activate the actuator 140 and selectively deploy the biosensor 128. Towards this end, the implantation device 120 may be provided with a handle assembly (not shown) associated with the actuator 140, the actuator 140 being controllable by manipulation of the handle assembly. In another preferred embodiment the actuator includes a hydraulic injection system that delivers fluid through the second lumen 130 in order to actively deploy the biosensor 128 out of the recess 126.

In order to retain the biosensor 128 within the recess 126 while the catheter 122 is guided to the implantation site, a thin adhesive film 129 at least partially covers the recess 126. The film 129 is easily ruptured or displaced when the actuator 140 deploys the biosensor 128. Alternately, the film 129 can be formed from a soluble material that will dissolve when a solution is dispensed through the lumen 124.

Figure 6:
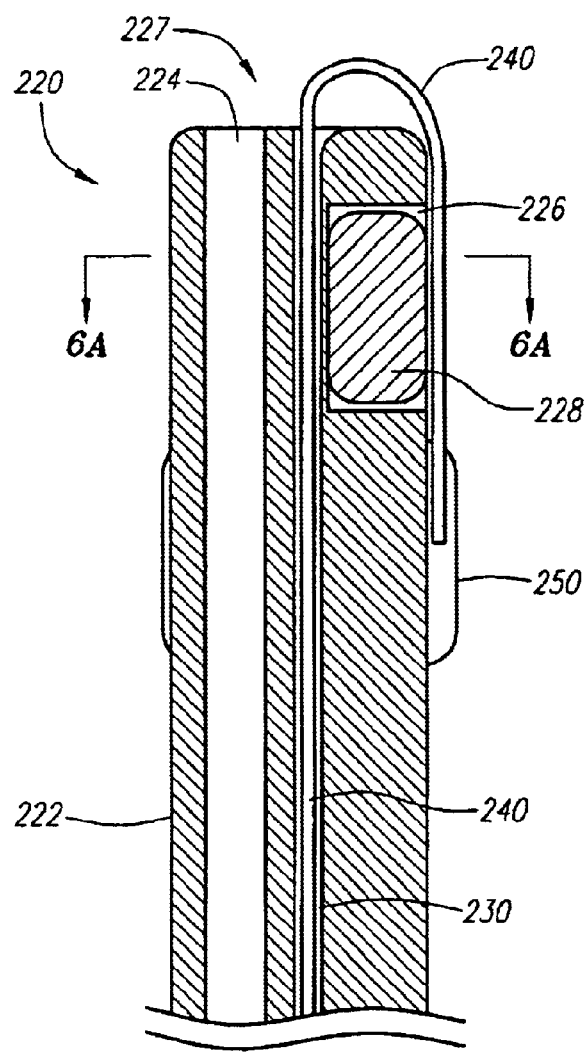
FIG. 6 is a cut-away side view of a distal portion of yet another further preferred embodiment of an implantation device constructed in accordance with the present invention.
Figure 6A:
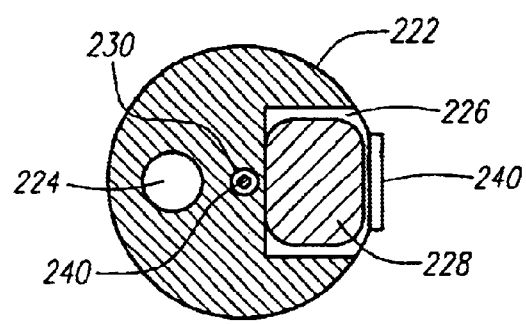
FIG. 6A is a cut-away cross section of the implantation device, taken along lines A—A of FIG. 6.

By way of further illustration, FIGS. 6 and 6A show yet another preferred bio sensor implantation device 220, constructed in accordance with the present invention. The implantation device 220 comprises an elongate catheter 222 including a guide wire lumen 224, a recess 226 for housing a biosensor 228, and an actuator in the form of a retractable sheath 240.

In particular, the sheath 240 is operative to retain and protect the biosensor 228 within the recess prior to deployment of the biosensor 228 at a selected implantation site. The sheath 240 extends through a second lumen 230 of the catheter 222 and extends from a distal end opening 227, wherein a distal portion of the sheath 240 is folded back over the catheter 222, at least partially covering the recess 226 to retain the biosensor 228 therein. A proximal portion of the sheath (not shown) extends to a proximal end of the catheter 222, enabling a user to retract the sheath 240 (e.g., with a handle assembly) and release the biosensor 228 from the recess 226. Alternatively, the proximal end of the sheath 240 is attached to the handle assembly with a wire. As the sheath 240 is retracted back into the distal opening 227, the recess 226 is no longer obstructed, whereby the biosensor 228 is "passively" deployed from the recess 226 into the implantation site.

The sheath 240 is preferably formed from a material with a low coefficient of friction, such as perfluoropolymers (e.g., PTFE, ePTFE, FEP, or polyurethane) with a wall thickness of less than 0.2 mm. The sheath may have a generally rectangular or triangular shape, such that it only covers a side of the catheter 222 having the recess 226. Alternately, the sheath 240 may have a tubular shape (e.g., such as a sausage casing), and is folded back over the entire circumference of the catheter 222 rather than just over the side having the recess 226. A clamping sleeve 250 is disposed about an outer circumference of the catheter 222 to secure the distal end of the sheath 240 over the recess 226, as the catheter 22 is guided to the implantation site. The clamping sleeve 250 can be made of an elastic material (such as silicone), or a shrink tube (such as FEP, PVC), preferably with a wall thickness of less than 0.15 mm. As will be appreciated by those skilled in the art, many other types of mechanical fasteners are possible for securing the sheath 240 over the recess 226, and are contemplated within the scope of the invention.

Figure 7:
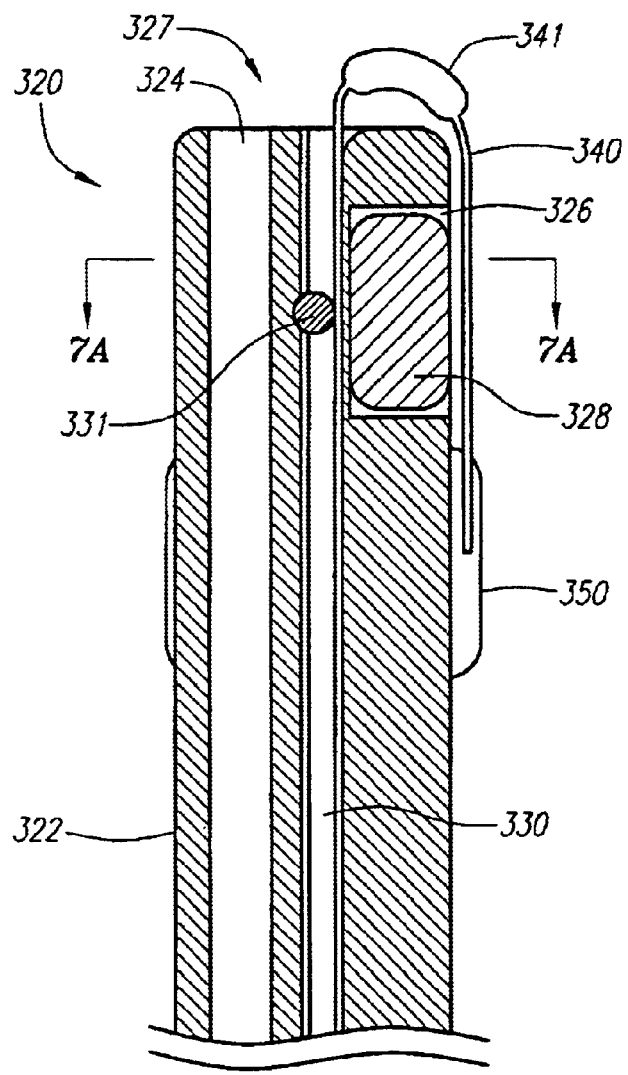
FIG. 7 is a cut-away side view of a distal portion of a still another preferred embodiment of an implantation device constructed in accordance with the present invention.
Figure 7A:
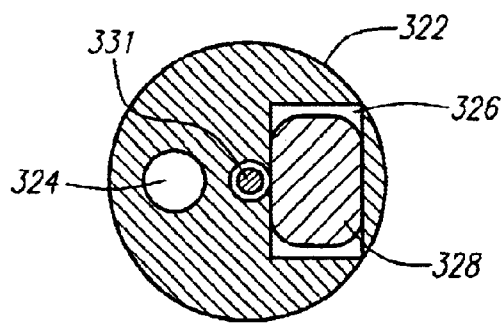
FIG. 7A is a cut-away cross section of the implantation device, taken along lines A—A of FIG. 7.

By way of still further illustration, FIGS. 7 and 7A show yet another preferred biosensor implantation device 320, constructed in accordance with the present invention. The implantation device 320 comprises an elongate catheter 322 including a guide wire lumen 324, a recess 326 for housing a biosensor 328, and an actuator in the form of a retractable filament 340.

In particular, the filament 340 is operative to retain the biosensor 328 in the recess 326 prior to its deployment at an implantation site. A distal portion of the filament 340 extends through a second lumen 330 of the catheter 322 and out of a distal end opening 327, where it is folded back over the recess 326 to retain the biosensor 328 therein. A proximal portion of the filament (not shown) extends to a proximal end of the catheter 322, enabling a user to retract the filament 340 (e.g., with a handle assembly), and release the biosensor 328 from the recess 326.

The filament 340 is preferably formed from a material with a low coefficient of friction such as perfluoropolymers (e.g., PTFE, ePTFE, FEP, or polyurethane) with a wall thickness of less than 0.2 mm. A clamping sleeve 350 is circumferentially disposed about the catheter 322 to secure the distal end of the filament 340 during delivery of the device 320 to the implantation site. The clamping sleeve 350 can be made of an elastic material (such as silicone), or a shrink tube (such as FEP, PVC), preferably with a wall thickness of less than 0.15 mm. Again, as will be appreciated by those skilled in the art, many other types of mechanical fasteners are possible for securing the filament 340 over the recess 326, and are contemplated within the scope of the invention.

In accordance with the features of the preferred implantation device 320, disposed within the second lumen 330 and adjacent the recess 326, is a protrusion 331 that restricts the inner diameter of the lumen 330 at a localized area. The distal end of the filament 340 includes a thickened portion 341 positioned such that the action of retracting the filament 340 causes the thickened portion 341 to pass through the portion of the lumen 330 restricted by the protrusion 331, thereby displacing the biosensor 328 from the recess 326.

As will be apparent to those skilled in the art, the exact positioning of the protrusion 331 may vary. For example, the filament 340 may be positioned to pass between the protrusion 331 and wall of the recess 326 (as shown in FIG. 7), with the gradually locally widened portion of the filament 341 causing ejection of the biosensor 328 from the recess 326. Alternatively, the protrusion 331 may be positioned adjacent the wall of the recess 326, or may actually comprise a thickened portion of the recess wall, such that retraction of the thickened portion of the filament 341 causes the protrusion 331 to actively eject the biosensor 328 from the recess 326.

Figure 8:
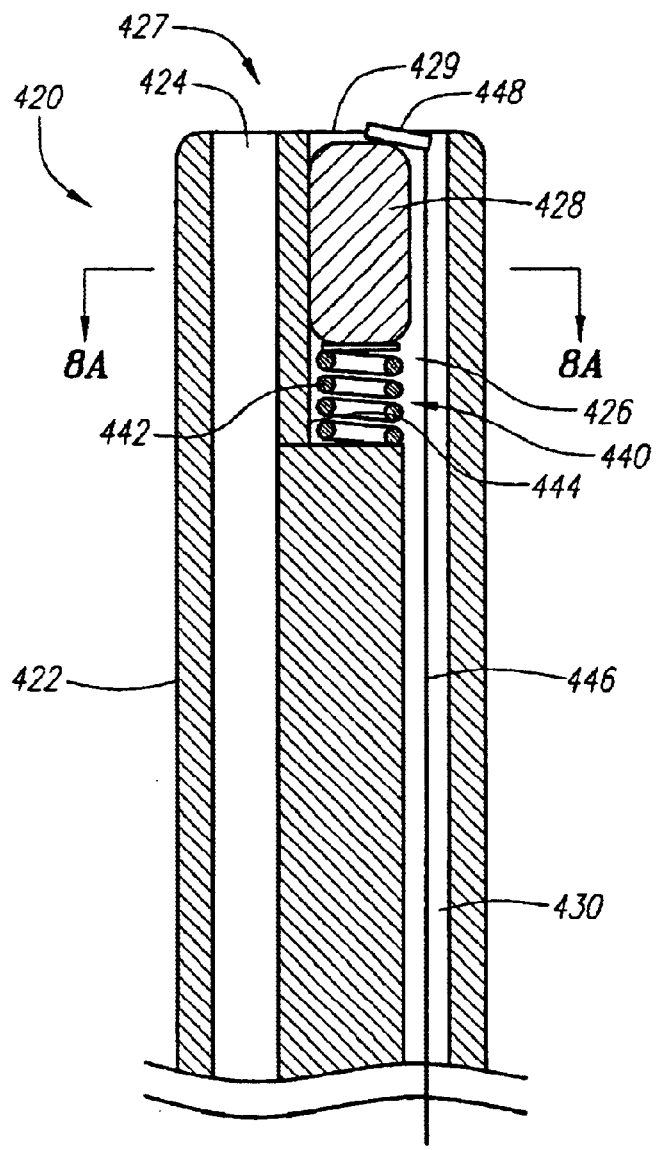
FIG. 8 is a cut-away side view of a distal portion of a still further preferred embodiment of an implantation device constructed in accordance with the present invention.
Figure 8A:
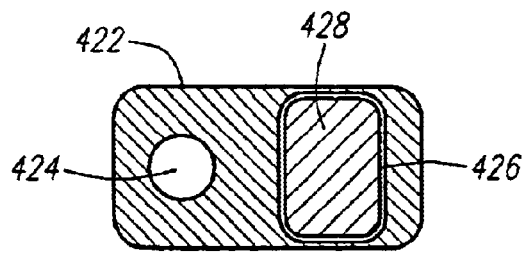
FIG. 8A is a cut-away cross section of the implantation device, taken along lines A—A of FIG. 8.

By way of still further illustration, FIGS. 8 and 8A show yet another preferred biosensor implantation device 420, constructed in accordance with the present invention. The implantation device 420 comprises an elongate catheter 422 including a guide wire lumen 424, a cavity 426 for housing a biosensor 428, and an actuator 440.

In accordance with the features of preferred implantation device 420, the actuator 440 includes a biased spring 442 positioned in the recess 426, and a plunger 444 that rests on a distal end of the spring 442. The plunger 444 includes an enlarged surface for ejecting the biosensor 428 from the recess 426. Extending through a second lumen 430 is a retention wire 446 that includes a retention flange 448 on its distal end. As the catheter 422 is guided to an implantation site in a patient's body, the retention flange 448 holds the biosensor 428 in place within the recess 426, counteracting the force created by the biased spring 442. The retention wire extends to a proximal end of the catheter 422 (not shown), enabling a user to release the retention flange 448 (e.g., with a handle assembly) and selectively deploy the biosensor 428.

In order to retain the biosensor 428 within the recess 426 while the catheter 422 is guided to the implantation site, a thin adhesive film 429 at least partially covers the recess 426. The film 429 is easily ruptured when the actuator 440 deploys the biosensor 428. Alternately, the film 429 can be formed from a soluble material that will dissolve when a solution is dispensed through the guide wire lumen 424.

An implantation device constructed in accordance with the present invention is preferably used in conjunction with a method of delivering a biosensor to an implantation site in a body wherein a catheter with a biosensor disposed in a distal recess or cavity is introduced into the body until the recess is positioned at the implantation site, and the biosensor is then ejected from the recess into the implantation site. Alternately, an actuator can be placed in, or adjacent to, the recess, and ejecting the biosensor is accomplished with the actuator. If a membrane is included on a distal end of the implantation device, the ejection of the biosensor causes the biosensor to be pushed through the membrane and into the implantation site.

In another method of using an implantation device for delivering a biosensor to an implantation site in a body, where the implantation device comprises an elongate catheter having a distally located recessed area configured to house the biosensor, and a retractable retaining element configured to retain the biosensor in the recessed area, the method comprises introducing the catheter into the body, with the biosensor retained in the recessed area by the retaining element, until the recessed area is positioned at the implantation site, and retracting the retaining element so that the biosensor may move freely from the recessed area into the implantation site.

In still a further method of using an implantation device for delivering a biosensor to an implantation site in a body, the implantation device comprising an elongate catheter having a distally located recess configured to at least partially house the biosensor, a retractable cover member configured to retain the biosensor within the recess, and an actuator configured to displace the biosensor from the recess, the method comprises introducing the catheter into the body with the biosensor retained within the recess by the cover member, until the recess is positioned at the implantation site, retracting the cover member to allow passage of the biosensor from the recess, and ejecting the biosensor from the recess with the actuator.

Figure 9:
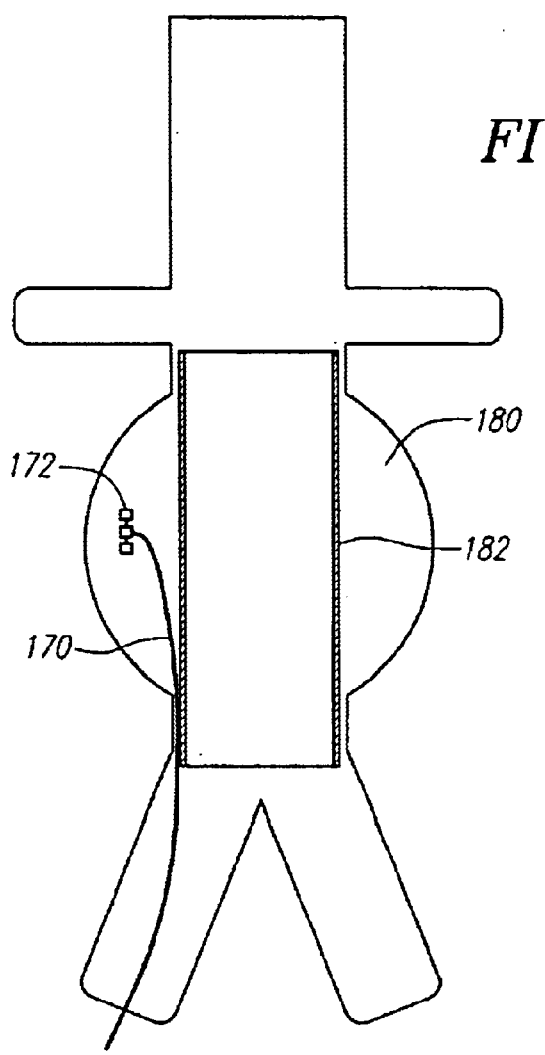
FIGS. 9 and 10 depict the use of a preferred implantation device for deploying one or more biosensors in an abdominal aortic aneurysm in conjunction with placement of a stent graft.
Figure 10:
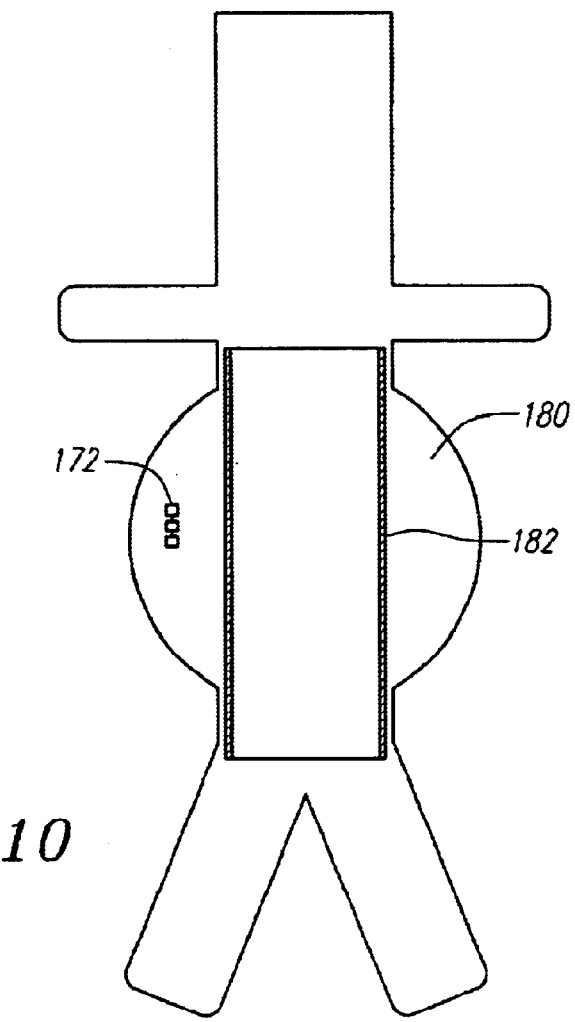

As depicted in FIGS. 9 and 10, each of the above methods and implantation devices (generally referred to by device 170) can be used to deploy one or more biosensors 172 in an abdominal aortic aneurysm 180 in conjunction with the placement of a stent graft 182.

While preferred embodiments and applications of the present invention have been shown and described, as would be apparent to those skilled in the art, many modifications and applications are possible without departing from the inventive concepts herein. For example, many other retaining mechanisms are possible beyond the disclosed adhesive film and retractable sheath and filament embodiments for securing one or more biosensors in a delivery catheter until they are to be deployed at an implantation site, and all such other mechanisms are contemplated within the scope of the invention.

Thus, the scope of the disclosed invention is not to be restricted except in accordance with the appended claims.

What is claimed is:

1. An implantation device for delivering a biosensor to an implantation site in a body, comprising:
   an elongate catheter comprising a recess configured to carry the biosensor while the catheter is guided to the implantation site;
   wherein the recess comprises a disposed indentation etched or otherwise formed on only one side of the catheter.

2. A device for delivering a biosensor to an implantation site in a body, comprising:
   an elongate catheter comprising a recess configured to carry the biosensor while the catheter is guided to the implantation site; and
   a retaining element configured to retain the biosensor in the recess;
   wherein the retaining element comprises a retractable cover member inserted through a distal opening of the catheter.

3. The implantation device of claim 2, wherein the recess comprises a longitudinally disposed indentation formed in a side of the catheter.

4. The implantation device of claim 2, wherein the recess comprises a cavity formed in a side wall of the catheter.

5. The implantation device of claim 2, wherein the recess comprises a cavity formed in a distal tip of the catheter.

6. The implantation device of claim 2, wherein the retractable cover member comprises a thin membrane.

7. The implantation device of claim 2, wherein the retractable cover member comprises a retractable filament inserted through a distal opening of the catheter.

8. The implantation device of claim 2, further comprising a clamping mechanism adapted to secure the retaining element against the catheter.

9. The implantation device of claim 8, wherein the clamping mechanism comprises a sleeve circumferentially attached to the catheter.

10. The implantation device of claim 2, further comprising an actuator, configured to eject the biosensor from the recess.

11. The implantation device of claim 10, wherein the actuator comprises a piston.

12. The implantation device of claim 10, wherein the actuator comprises a spring.

13. The implantation device of claim 10, wherein the actuator comprises a hydraulic injector.

14. The implantation device of claim 2, wherein the retractable cover member comprises a retractable sheath.

15. An implantation device for delivering a biosensor to an implantation site in a body, comprising:
   an elongate catheter comprising a recess configured to carry the biosensor while the catheter is guided to the implantation site;
   and an actuator disposed in, or adjacent to, the recess, the actuator configured to eject the biosensor from the recess;
   wherein the actuator comprises a protrusion located in, or adjacent to, the recess, the protrusion positioned to displace biosensor from the recess.

16. The implantation device of claim 13, further comprising a handle assembly associated with the actuator, the actuator being controllable by manipulation of the handle assembly.

17. An implantation device for delivering a biosensor to an implantation site in a body, comprising:

an elongate catheter having a recess formed in a distal end, the recess configured to carry the biosensor without significantly increasing the profile of the catheter distal end;

a retaining element configured to retain the biosensor in the recess; and an actuator disposed in, or adjacent to, the recess, the actuator configured to eject the biosensor from the recess;

wherein the retaining element comprises a retractable cover member extending out of a distal opening of the catheter.

18. The implantation device of claim 17, wherein the retractable cover member comprises a thin membrane at least partially covering the cavity.

19. The implantation device of claim 17, wherein the retractable cover member comprises a retractable filament inserted through a lumen of the catheter adjacent the recess, the filament extending out of a distal opening of the catheter.

20. The implantation device of claim 19, wherein the actuator comprises a protrusion located in, or adjacent to, the recess, and wherein a distal portion of the filament has a relatively thick profile, such that the protrusion is displaced into the recess by the distal portion as the filament is retracted through the lumen.

21. The implantation device of claim 19, wherein the actuator comprises a protrusion located adjacent to a wall of the recess, and wherein a distal portion of the filament has a relatively thick profile, such that the protrusion deflects the filament against the wall as the filament is retracted through the lumen, causing the biosensor to be displaced from the recess.

22. The implantation device of claim 17, further comprising a clamping mechanism adapted to secure the retaining element against the catheter, while the catheter is guided to the implantation site.

23. The implantation device of claim 22, wherein the clamping mechanism comprises a sleeve circumferentially attached to the catheter.

24. The implantation device of claim 17, wherein the retractable cover member comprises a retractable sheath.

25. A method for delivering a biosensor to an implantation site in a body, comprising:

introducing a catheter into the body, the catheter having a recessed area that houses a biosensor, a distal opening, and a retaining element that is inserted through the distal opening, the retaining element being configured to retain the biosensor in the recessed area;

advancing the catheter until the recessed area is positioned at the implantation site; and retracting the retaining element so that the biosensor may move freely from the recessed area into the implantation site.

26. The method of claim 25, further comprising ejecting the biosensor from the recess.

27. The method of claim 25, wherein the implantation site is either an abdominal aortic aneurysm, in the iliac of a bifurcated abdominal aortic aneurysm, a thoracic aortic aneurysm, or any combination of the above.

28. The method of claim 25, wherein the catheter is guided to the implantation site in conjunction with the delivery of a stent graft.

29. The method of claim 25, wherein the biosensor comprises a sensor selected from the group consisting of a pressure sensor, a temperature sensor, a position sensor, a tactility sensor, an electrical impedance sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electrical energy sensor, an electromagnetic field sensor, a chemical sensor, an ionic sensor, and an enzymatic sensor.

30. A method for delivering a biosensor to an implantation site in a body, comprising:

introducing a catheter into the body, the catheter having a recessed area that houses a biosensor, a distal opening, a retaining element that is inserted through the distal opening and is configured to retain the biosensor in the recessed area, and an actuator configured to displace the biosensor from the recess;

advancing the catheter until the recess is positioned at the implantation site;

retracting the cover member to allow passage of the biosensor from the recess; and ejecting the biosensor from the recess into the implantation site with the actuator.

31. A method performed in conjunction with the method of claim 30, comprising:

inserting a stent graft in the implantation site.

* * * * *